US010588495B2

(12) United States Patent
Simmons et al.

(10) Patent No.: US 10,588,495 B2
(45) Date of Patent: Mar. 17, 2020

(54) BRAKE MECHANISM OF A STEERABLE CATHETER (71) Applicant: Cook Medical Technologies LLC, Bloomington, IN (US)

(72) Inventors: Victor Simmons, Mt. Airy, NC (US); Travis E. Dillon, Winston-Salem, NC (US)

(73) Assignee: Cook Medical Technologies LL, Bloomington, IN (US)

( * ) Notice: Subject to any disclaimer, the term of this patent is extended or adjusted under 35 U.S.C. 154(b) by 329 days.

(21) Appl. No.: 15/655,017

(22) Filed: Jul. 20, 2017

(65) Prior Publication Data

US 2018/0028048 A1 Feb. 1, 2018

Related U.S. Application Data (60) Provisional application No. 62/367,910, filed on Jul. 28, 2016, provisional application No. 62/367,918, filed on Jul. 28, 2016, provisional application No. 62/367,938, filed on Jul. 28, 2016, provisional application No. 62/367,959, filed on Jul. 28, 2016.

(51) Int. Cl.
*A61B 1/005* (2006.01)
*A61M 25/01* (2006.01)
*A61M 25/00* (2006.01)

(52) U.S. Cl.
CPC .......... *A61B 1/0051* (2013.01); *A61B 1/0052* (2013.01); *A61B 1/0057* (2013.01); *A61M 25/0026* (2013.01); *A61M 25/0028* (2013.01); *A61M 25/0105* (2013.01); *A61M 25/0136* (2013.01); *A61M 25/0147* (2013.01); *A61M 2025/004* (2013.01)

(58) Field of Classification Search
CPC .......... A61M 25/0105; A61M 25/0133; A61M 25/0136; A61M 25/0147; A61M 2025/015; A61M 2025/0161; A61B 1/00066; A61B 1/00068; A61B 1/005; A61B 1/0051; A61B 1/0052; A61B 1/0053; A61B 1/0057
See application file for complete search history.

(56) References Cited

U.S. PATENT DOCUMENTS 3,557,780 A 1/1971 Hachioji-shi
3,610,231 A 10/1971 Takahashi et al.
(Continued)

FOREIGN PATENT DOCUMENTS

EP 0306723 3/1989
EP 0341719 11/1989
(Continued)

*Primary Examiner* — Kami A Bosworth
(74) *Attorney, Agent, or Firm* — Brinks Gilson & Lione (57) ABSTRACT A steerable catheter includes a brake mechanism with a knob mounted to a catheter handle body. The knob is rotatable around a knob axis, and the catheter handle body includes at least one steering control spool rotatable around a spool axis that is orthogonal to the knob axis. The knob contacts and rotates in a limited arc along a recessed handle body surface between stop surfaces. A frictional braking element in mechanical communication, along the knob axis, with the knob is disposed adjacent the at least one steering control spool and actuatable into and out of contact with a contact surface of the at least one spool upon rotation of the knob around the knob axis.

20 Claims, 7 Drawing Sheets (56) References Cited

U.S. PATENT DOCUMENTS

| | | |
|---|---|---|
| 4,078,555 A | 3/1978 | Takahashi |
| 4,461,282 A | 7/1984 | Ouchi et al. |
| 4,566,437 A | 1/1986 | Yamaguchi |
| 4,617,914 A | 10/1986 | Ueda |
| 4,825,850 A | 5/1989 | Opie et al. |
| 4,942,866 A | 7/1990 | Usami |
| 5,014,685 A | 5/1991 | Takahashi |
| 5,329,887 A | 7/1994 | Ailinger et al. |
| 5,479,930 A | 1/1996 | Gruner et al. |
| 5,507,717 A | 4/1996 | Kura et al. |
| 5,575,755 A | 11/1996 | Krauter et al. |
| 5,762,067 A | 6/1998 | Dunham et al. |
| 5,810,715 A | 9/1998 | Moriyama |
| 5,888,192 A | 3/1999 | Heimberger |
| 6,533,783 B1 | 3/2003 | Tollner |
| 6,599,265 B2 | 7/2003 | Bon |
| 6,648,875 B2 | 11/2003 | Simpson et al. |
| 6,656,111 B2 | 12/2003 | Fujii et al. |
| 6,673,012 B2 | 1/2004 | Fujii et al. |
| 7,682,358 B2 | 3/2010 | Gullickson et al. |
| 7,846,089 B2 | 12/2010 | Maruyama |
| 8,287,448 B2 | 10/2012 | Schaaf |
| 8,449,530 B2 | 5/2013 | Bacher et al. |
| 8,523,808 B2 | 9/2013 | Selkee |
| 8,608,649 B2 | 12/2013 | McWeeney et al. |
| 8,679,004 B2 | 3/2014 | Konstorum |
| 8,808,168 B2 | 8/2014 | Ettwein et al. |
| 8,808,169 B2 | 8/2014 | Macnamara et al. |
| 8,864,656 B2 | 10/2014 | Konstorum |
| 8,992,470 B2 | 3/2015 | Barenboym et al. |
| 9,155,865 B2 | 10/2015 | Golden et al. |
| 9,199,061 B2 | 12/2015 | Selkee |
| 9,380,930 B2 | 7/2016 | Oskin et al. |
| 2002/0019591 A1 | 2/2002 | Bon |
| 2002/0099266 A1 | 7/2002 | Ogura et al. |
| 2003/0236493 A1 | 12/2003 | Mauch |
| 2006/0167343 A1* | 7/2006 | Peszynski ............ A61B 1/0052 600/146 |
| 2013/0012781 A1* | 1/2013 | Kaneko ............... A61B 1/00066 600/148 |
| 2014/0088497 A1 | 3/2014 | Campbell et al. |
| 2014/0275763 A1 | 9/2014 | King et al. |
| 2015/0099927 A1 | 4/2015 | Sadoughi |
| 2015/0119800 A1 | 4/2015 | Neoh et al. |
| 2015/0359415 A1 | 12/2015 | Lang et al. |
| 2015/0366435 A1 | 12/2015 | Williams |
| 2016/0231556 A1* | 8/2016 | Yasunaga ........... G02B 23/2476 |

FOREIGN PATENT DOCUMENTS

| | | |
|---|---|---|
| EP | 1350471 | 10/2003 |
| EP | 0754429 | 9/2004 |
| EP | 2106751 | 10/2009 |
| EP | 2220991 | 9/2011 |
| EP | 2594307 | 5/2013 |
| EP | 2865319 | 4/2015 |
| EP | 2319388 | 10/2015 |
| EP | 2799001 | 12/2015 |
| JP | 2005/160790 | 6/2005 |
| WO | WO 2004/000405 | 12/2003 |
| WO | WO 2009/140288 | 11/2009 |
| WO | WO 2010/140080 | 12/2010 |
| WO | WO 2014/115068 | 7/2014 |
| WO | WO 2014/186519 | 11/2014 |

\* cited by examiner

BRAKE MECHANISM OF A STEERABLE CATHETER

CROSS-REFERENCE TO RELATED APPLICATIONS

This application is a non-provisional application which claims priority to U.S. provisional application Ser. Nos. 62/367,910; 62/367,918; 62/367,938; and 62/367,959; all filed Jul. 28, 2016, each of which is incorporated by reference herein in its entirety.

TECHNICAL FIELD

Embodiments disclosed herein generally relate to steerable catheters, including endoscopes. More particularly embodiments disclosed herein relate to a structures and methods for a brake that will lock into place actuation elements of a steerable catheter.

BACKGROUND

Deflecting catheters, also referred to as steerable catheters are used in a variety of medical and non-medical procedures. In diagnostic and therapeutic medical procedures, a steerable catheter provides an operator (e.g., physician) with the ability to articulate the distal tip of the catheter in order to travel through constrained and/or tortuous anatomy, and/or to direct the distal catheter tip in a particular direction. Similar mechanisms are used in medical and nonmedical endoscopes to steer them to a target site and to orient a device portion (e.g., including a camera or other visualization means) in a desired direction.

Figure 1:
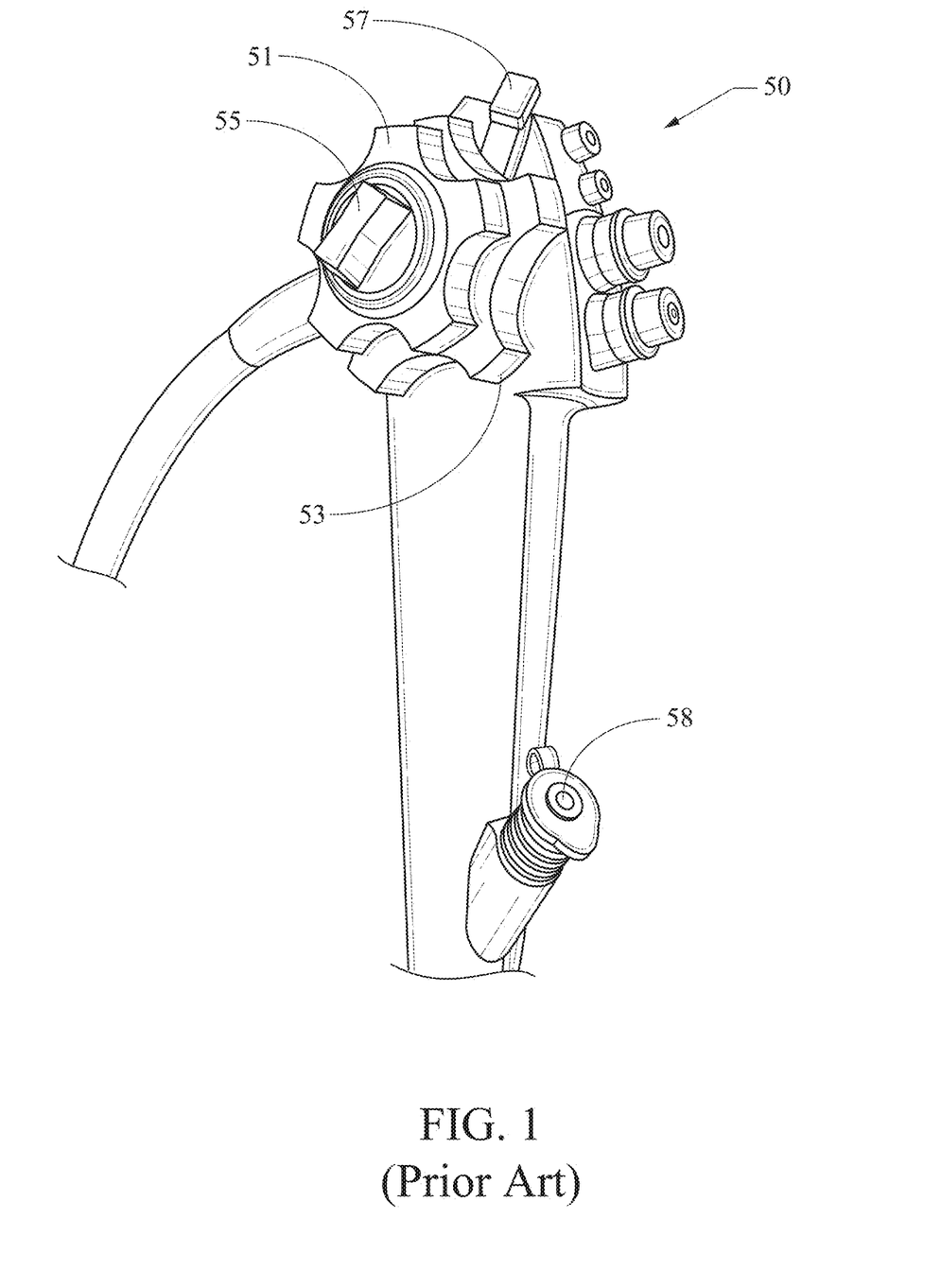
FIG. 1 shows a prior steerable catheter device.

In a typical design, control wires are manipulably attached at a proximal end of the device, and also attached at or near a distal end of the device. Such a configuration operates by manipulating one or more of the control wires to increase and/or decrease a generally longitudinal force on the distal device end that will deflect it in a desired direction. As described with reference to an existing steerable endoscopic camera device 50 of FIG. 1, the control wires may be actuated by rotation of control wheels 51, 53. Each control wheel can be rotated to operate a control wire or pair of control wires in a manner exerting push/pull tension on a deflectable distal device portion (not shown, but well-known in the art) to deflect that portion along a first plane, while the other control wheel operates similarly to deflect that portion along a second plane intersecting (e.g., orthogonal to) the first plane. At times, it is desirable to lock that distal device portion into a particular deflected orientation (e.g., so that the operator may execute another task requiring releasing hand contact with one or both control wheels). The illustrated device 50 includes a first brake for the first control wheel 51, with a twistable knob 55 for locking/unlocking an internal brake mechanism that operates along the central rotational axis of the first control wheel 51. The illustrated device 50 includes a second brake for the second control wheel 51, with a lever 57 for locking/unlocking an internal brake mechanism that operates by exerting a braking engagement along the central rotational axis of the second control wheel 53. One or both brake controls 55, 57 require a user to change his/her grip for actuation. Other examples of brake mechanisms are described and illustrated in, for example, U.S. Pat. Nos. 8,864,656; 8,808,168; 8,608,649; 8,641,604; 8,366,604; 6,673,012; and 5,507,717.

It is be desirable to provide braking means that allow a user to "lock" into place the wire-operating elements within the control handle in a manner that will hold the distal end of the steerable catheter in a user-determined deflected or non-deflected orientation. Moreover, there is a need for such a braking means that is operable without a user needing to release other control elements of the steerable catheter, and which may simultaneously brake or even lock more than one control wheel/wire element to as to control (that is reduce or eliminate) deflection of the distal end portion through/along all planes.

BRIEF SUMMARY

In one aspect, embodiments disclosed herein may include a steerable catheter with a braking mechanism, where a frictionally-engaging braking element engages actuation/control spools of the steerable catheter in a lockable manner that will inhibit (up to and including preventing) movement of a distal end catheter portion out of a selected deflected conformation. The angle of force and the structures of the present embodiments differ from prior braking mechanisms including that the present embodiments use a brake-actuation axis that is orthogonal to (rather than coaxial or nearly coaxial with) a central rotational axis of control handles and spools of the steerable catheter.

In some embodiments of a steerable catheter with a braking mechanism, the steerable catheter includes a proximal handle body from which extends distally an elongate steerable catheter body with a deflectable distal catheter body end. The proximal handle body includes: at least a first control wheel in mechanical communication, via a first spool, with the distal catheter body end, where the at least a first control wheel and the first spool are rotatable around a common control wheel axis; a brake knob mounted rotatingly to the proximal handle body and configured to rotate around a brake knob axis that is non-coaxial with the control wheel axis; a brake arm in mechanical communication with the brake knob and disposed between the brake knob and the first spool, said brake arm including at least one spool-engagement surface; and ramped and planar handle body surfaces that complementarily interface with ramped and planar brake knob surfaces such that (i) in a first brake-actuation knob position the at least one spool-engagement surface does not contactingly engage the first spool, and (ii) in a second brake-actuation knob position the at least one spool-engagement surface does contactingly engage the first spool.

In another aspect, embodiments disclosed herein may include a steerable catheter with a brake mechanism that includes a knob mounted to a catheter handle body, said knob being rotatable (relative to the handle body) around a knob axis; where the catheter handle body includes at least one steering control spool rotatable around a spool axis that is orthogonal to the knob axis; a handle ramped surface separated from a handle stop-surface, where a handle-contacting knob surface is movable across the handle ramped surface and is not movable past the handle stop-surface; and a frictional braking element in mechanical communication (along the knob axis) with the knob, said braking element disposed adjacent the at least one spool and actuatable into and out of contact with a contact surface of the at least one spool upon rotation of the knob around the knob axis.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Generally, embodiments disclosed herein relate to a structure and system for securely attaching the proximal ends of control wires (including any kind of control fiber, regardless of construction material) to the control spool(s) of a steerable catheter. In the most preferred embodiments, the structure and system include means for tuning—that is finely adjusting—relative tension of each of those control wires between the proximal end and a permanently/securely attached distal control wire end attached more distally within the steerable device. Too much or too little tension in each of the control wires (on its own, and more particularly in relation to the other control wire(s)) can cause premature or otherwise undesired deflection of the steerable device and/or may cause the steerable device to operate in a manner that is not desired or predictable. During assembly of a steerable catheter device, the system can be used to take up slackness one or all control wires.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object. The terms "about," "generally," "substantially," and other generalizing terms, when used with reference to any volume, dimension, proportion, or other quantitative value is intended to communicate a definite and identifiable value within the standard parameters and variations that would be understood by one of skill in the art, and should be interpreted to include at least any legal equivalents (same or substantially similar function, manner of operation, and result at the element and assembly levels), minor but functionally-insignificant variants, and encompassing a numerical range that includes at least mathematically significant figures (although not required to be as broad as the largest range thereof), as well as including physical embodiments that encompass normal variations in manufacturing tolerances.

The term "control wire" (including just "wire") is used herein to denote the elongate members that connect a control surface of a steerable catheter with a deflectable distal portion of the catheter, and it may include metallic, polymeric, and/or other materials including—by way of nonlimiting example—ultrahigh molecular weight polyethylene (UHMWPE) yarn (e.g., Dyneema™), aramid fibers, monofilament line, multifilament/multifilar cable, and/or other materials that preferably have high tensile strength with low longitudinal stretch so as to provide predictable operation behavior. Metallic control wires can include stainless steel, NiTi, and/or high carbon steel alloy "music wire". Various other polymers may also be used within the scope of the present disclosure. The wire shape may be round (circular or non-circular in transverse section), flat (including rectilinear or with flat surfaces in transverse section). With regard to the physical construction, it may also be braided and/or twisted and optionally may be fused along at least some lengthwise portions. Also, the wires can be coated: for example a low friction polymer coating may be used over a substrate (or as a construction material) in order to reduce dynamic friction within the device's wire lumen(s) so as to provide a more controlled, repeatable response to actuation than higher-friction materials. One preferred material includes UHMWPE braided fiber. With regard to distal attachment of the control wire(s), a multifilar, braided, or other structure is preferred, which may be at least partially frayed or otherwise partially disaggregated (e.g., in order to provide greater surface area than a unitary aggregated wire structure, as described further below).

One example of a control wire may include a 4×-50 Denier ultrahigh tenacity polyethylene braid having a very small outer diameter of about 0.18 mm (measured in accordance with ASTM D-1907); high strength (about 5.6 kg, and at least equal to or greater than 4.75 kg, measured in accordance with ASTM D-6775); low longitudinal stretch/elongation (about 5%, ±2%, measured in accordance with ASTM D-6775) (e.g., as available from Textile Development Associates Inc. of Brookfield, Conn.). Certain preferred control wire embodiments include or may even consist of high modulus fiber material that is nonconductive and/or substantially nonstretching. In one embodiment, a high modulus fiber control wire material may be braided. One such high modulus fiber material can be a High Molecular Density Polyethylene, a melt spun liquid crystal polymer fiber rope, or a spun para-aramid fiber polymer, or a high strength ceramic fiber. In some embodiments, a high modulus fiber control wire material may have a tensile strength in a range of about 300 ksi (2,000 MPa) to 1,500 ksi (10,400 MPa), and/or a tensile modulus in the range of about 5,000 ksi (35,000 MPa) to about 20,000 ksi (140,000 MPa).

One embodiment of a steerable catheter device 100 is described with reference to FIG. 2. The steerable catheter device 100 includes a proximal control handle body 102 with a steerable catheter body 104 extending distally therefrom (which may have a default straight linear configuration, and for which is illustrated only a deflected distal end terminal lengthwise portion). Various embodiments may include one or more different steering control means known in the art. This illustrated embodiment includes a pair of control wheels, with an outer control wheel 110 and an inner control wheel 130. As set forth in greater detail below (including with reference to FIGS. 2B-2C), the outer control wheel 110 is disposed in mechanical communication with a pair of control wires that are operable, upon wheel rotation, to deflect at least the end portion 160 of the catheter body 104 along a first plane, and the inner control wheel 130 is disposed in mechanical communication with another pair of control wires that are operable, upon wheel rotation, to deflect the catheter body 104 along a second plane that may be generally orthogonal to the first plane, and is at least somewhat offset from that first plane. Simultaneous or sequential operation of the outer and inner wheels 110, 130 preferably can deflect the distal end portion 160 of the catheter body 104 in any direction around a 360-degree circle defined generally by a circumference of the catheter.

Steering mechanisms using control wires are well-known in the art including in U.S. Pat. Pub. No. 2015/0366435 to Williams, which is incorporated herein by reference in its entirety. The overall control structure described is also well known in the steerable device art, including particularly the endoscope art, but those devices lack the currently disclosed finely-controlled mechanism for efficient and effective tensioning of control wires. Certain embodiments in keeping with the present disclosure may include at least one visualization element (as well as supporting hardware and/or software, not shown—but well-known in the art and readily understandable as using electrical and/or optical devices such as CCD, fiber optic, CMOS, etc.) for use of such embodiments as endoscopic devices including, for example, as a cholangioscope configured for use with and through a larger endoscope.

Figure 2A:
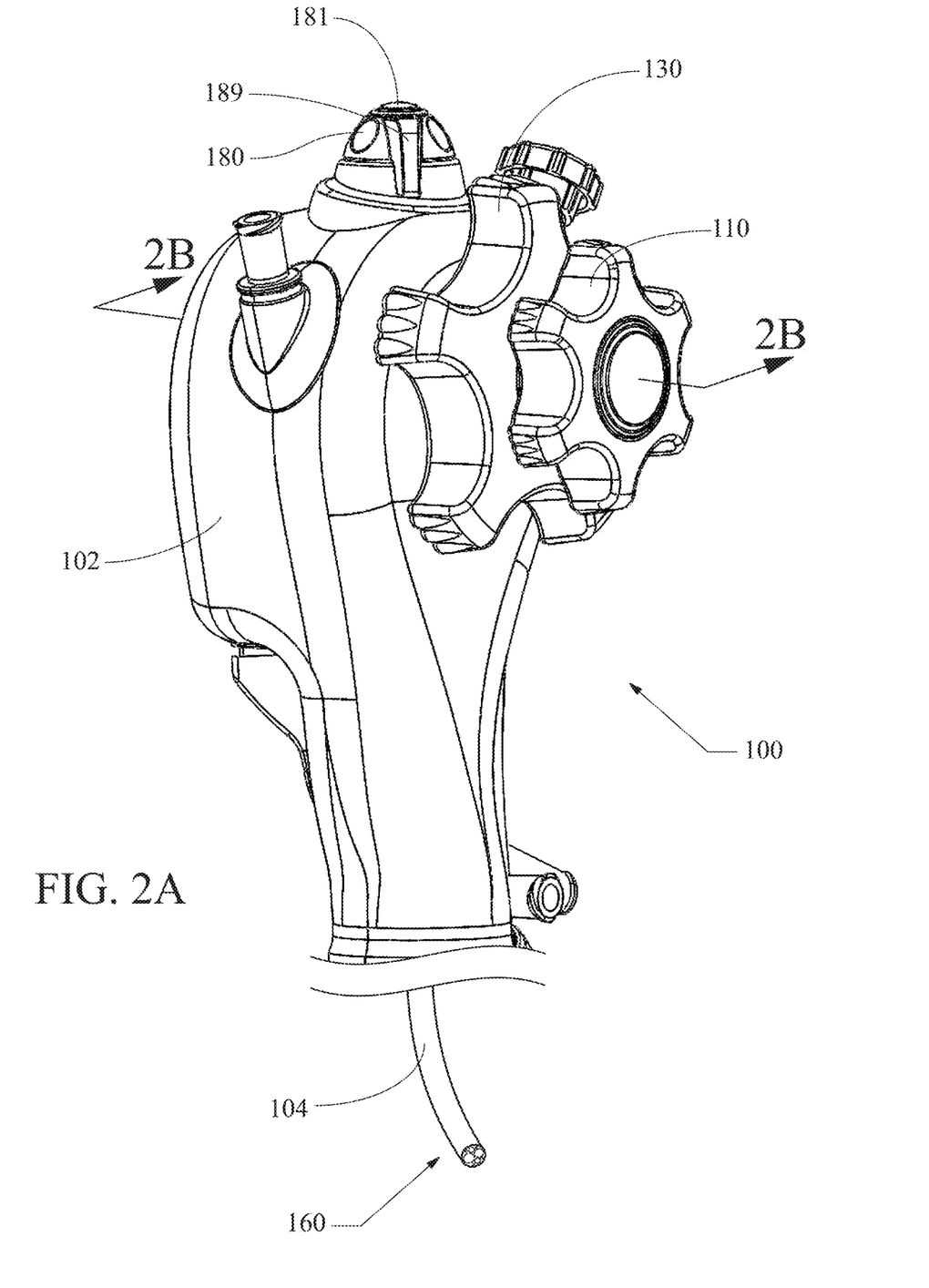
FIG. 2A shows a steerable catheter device embodiment handle and distal, deflected tip portion.
Figure 2B:
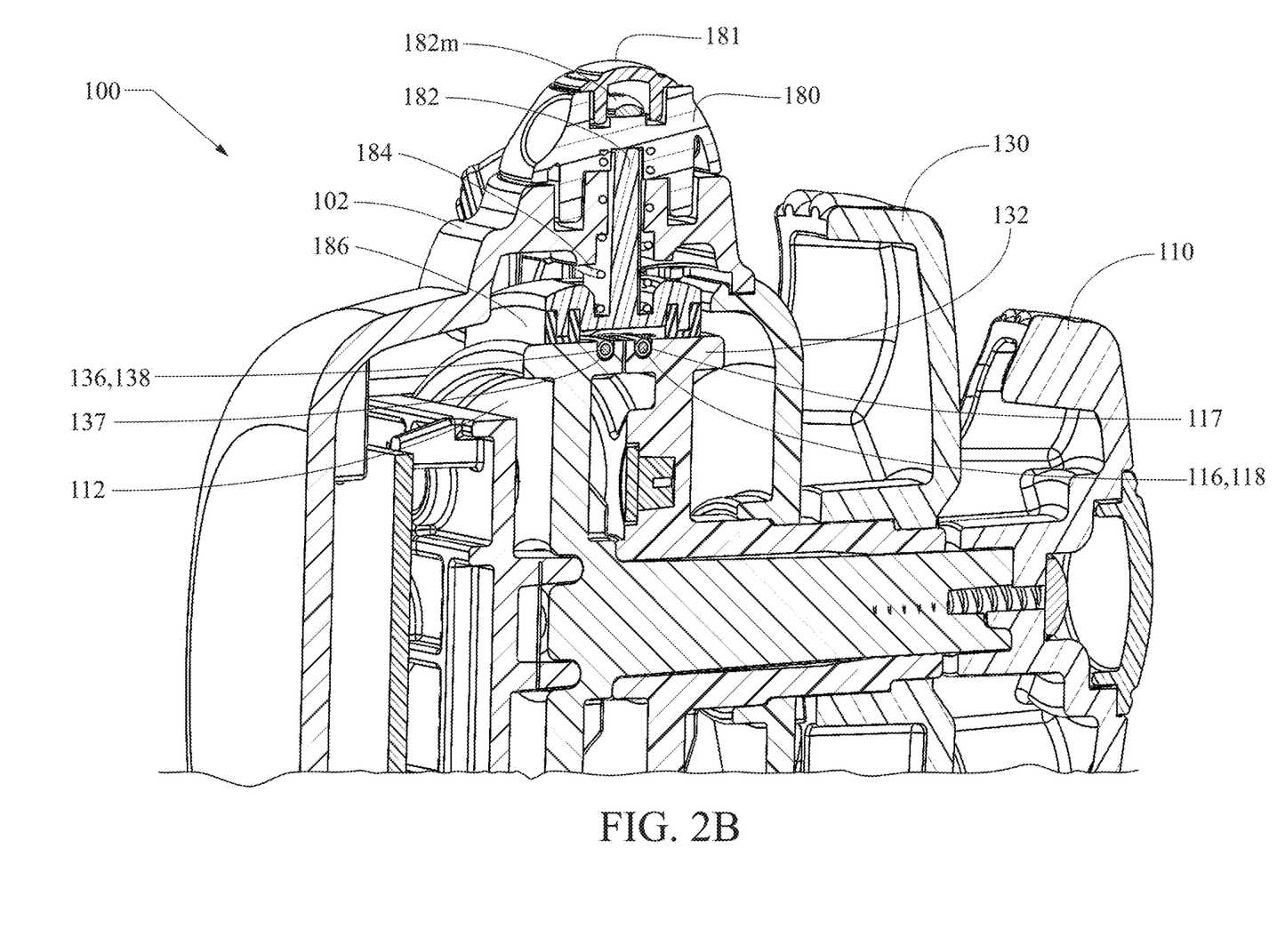
FIG. 2B shows a sagittal (vertical plane) section view of FIG. 2A taken along line 2B-2B.

A sagittal (vertical plane) section view of FIG. 2A taken along line 2B-2B is shown in FIG. 2B to illustrate the physical arrangement of components, from which those of skill in the art will understand the structures and functions described herein. A partially disassembled view of the control handle portion of the steerable catheter device 100 is shown in FIG. 2C, where a portion of the body 102, outer control wheel 110, and the inner control wheel 130 are removed, and the spool assemblies therein are shown in more detail. The outer control wheel 110 engages a shaft 114 of, and controls rotation of, an outer spool 112 around a common central rotational axis (that preferably is orthogonal to the generally circular handle and spool). The outer spool 112 includes a circumferential groove 115 around its outer circumferential surface, which groove 115 receives a tube 117 through which extend the proximal end regions of opposed first and second control fibers 116, 118. The outer spool 112 includes two gear-mounting apertures 121*a*, 121*b*, each of which receives and forms a rotation-permitting engagement with the split mounting end 152 of a gear 150. Each spool includes at least one face surface intersecting the spool axis (preferably having the major face congruent with a plane that is orthogonal to that spool rotational axis) and at least one circumferential surface that includes or is included by a contact surface that may frictionally be contacted by a brake mechanism.

The inner control wheel 130 engages a shaft 134 of, and controls rotation of, an inner spool 132. The inner spool 132 includes a circumferential groove 135 around its outer circumferential surface, which groove 135 receives a tube 137 through which extend the proximal end regions of opposed third and fourth control fibers 136, 138. The proximal end terminus of each control wire (not shown) is secured to its respective spool. Those of skill in the art will appreciate that rotary actuation of the outer control wheel 110 effects corresponding rotary actuation of the outer spool 112, while rotary actuation of the inner control wheel 130 effects corresponding rotary actuation of the outer spool 132, and that respective distal attachments of each control fiber to/in the distal end lengthwise portion 160 of the catheter body 104 will provide for controllable deflection.

Figure 2C:
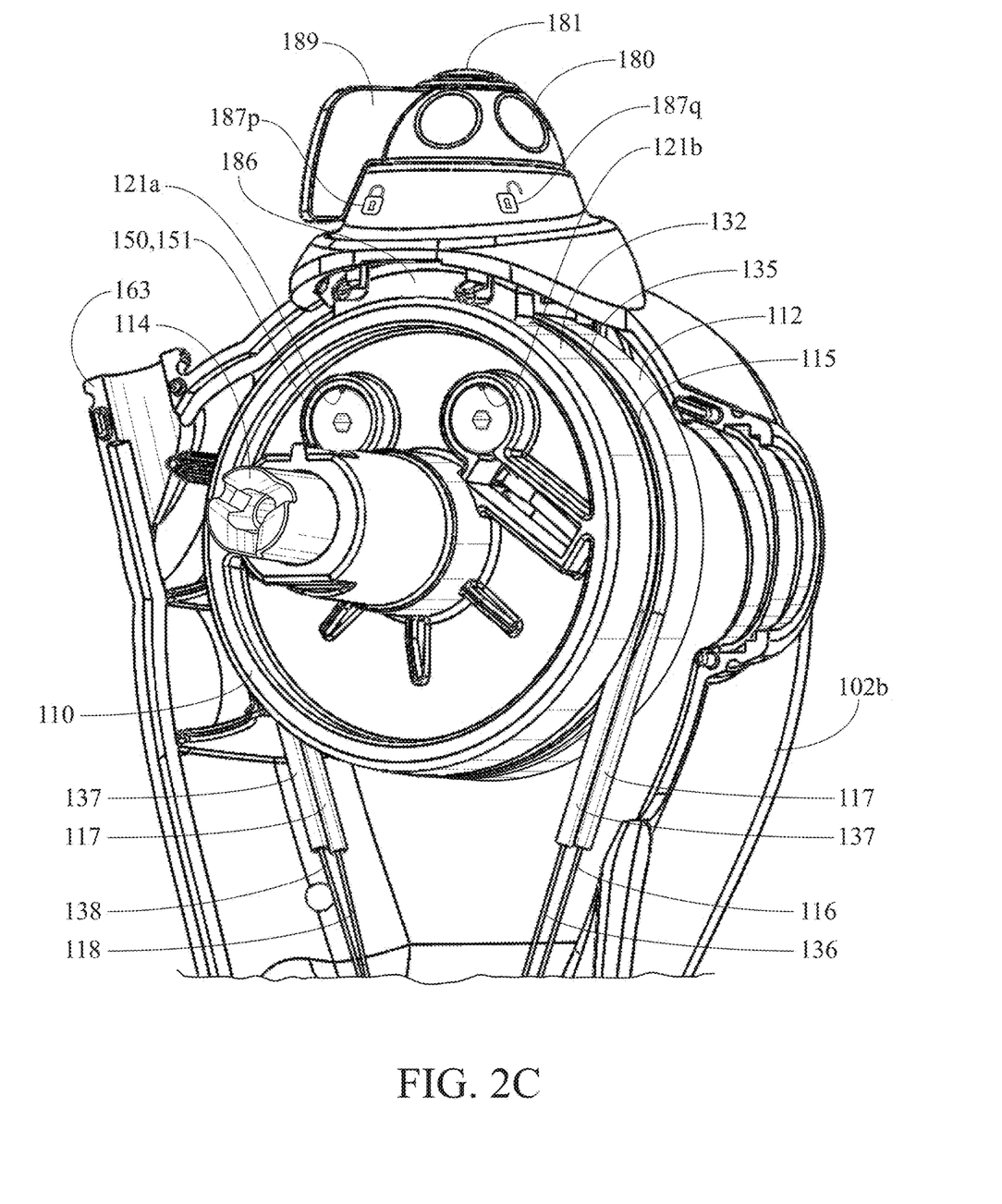
FIG. 2C is a partially disassembled perspective view of the embodiment of FIG. 2A.

As shown in FIGS. 2B and 2C, the outer spool shaft 114 extends through and beyond a central passage of the inner spool 132 and its shaft 134. A brake assembly is also depicted, including a brake-actuation knob 180 with cap 181, brake arm 182 including brake shoes 186 (which may be structurally and compositionally integral with or different than the rest of the arm), and a biasing element (illustrated here as a coil spring 184), elements of which are shown in FIGS. 3B-3D. In both FIGS. 2B and 2C, the illustrated brake assembly is shown as having two brake shoes 186 that serve as spool-engaging surfaces, where each one is shown in engaging contact with a respective one of the spools 112, 132. The biasing element 184 biases the brake arm 182 away from an inward-facing surface of the housing 102 toward/into this engaging contact, which preferably provides sufficient force to resist (up to and including to prevent) rotation of the spools relative to the brake arm 182 when fully engaged. More particularly, the spring (or other biasing element known or developed in the art) is selected and/or configured to exert a predetermined force when assembled. The contact shown is between the brake shoes 186 and an outer circumferential surface of the respective spools 112, 132. The axial direction of the biasing contact force preferably is at least substantially orthogonal to the central rotational axis of the spools 112, 132 and control wheels 110, 130, and is not coaxial with that central rotational axis (being at least, or greater than, about 30° off that central rotational axis).

In other embodiments, a single brake shoe, or an integrated same-material portion of the brake arm 182 may serve as the spool-engaging surface(s). In other embodiments, more or fewer elements may be used to contact and inhibit (up to and including preventing) movement of the spools by providing a predetermined force of the brake arm toward the spool—and preferably toward, and orthogonal with, the common rotational axis of the spool(s) and control wheel(s). This structure and functionality provides an operator of a steerable catheter to deflect the distal end portion to a desired conformation, then actuate the brake mechanism to inhibit spool movement and thereby hold that conformation while the operator frees up his/her hands to perform other tasks.

In the illustrated embodiment, a rotating knob 180 interfaces with the housing body 102 of the steerable catheter in order to actuate (that is, to engage and/or disengage) the brake mechanism relative to the spools. In this embodiment, the central rotational axis of the knob 180 is coaxial with the engagement/disengagement axis of the brake arm 182 and is orthogonal relative to the central rotational axis of the spools 112, 132 and control wheels 110, 130. The brake mechanism is configured so that rotation of the knob 180 in a first direction advances the brake arm toward the spools, and rotation in a second/opposite direction retracts the brake arm away from the spools. In the illustrated embodiment, the coil spring 184 provides biasing force against the brake arm 182 toward the spools. The knob 180 is attached to the brake arm 182 in a manner allowing the knob to rotate around the brake arm, but providing for fixed attachment and connected movement of the brake arm together with the knob along the longitudinal axis of the brake arm away from the spools. This attachment may be effected by a threaded connector (182*m* in FIG. 2B, disposed through a knob aperture 180*m*) or other means that preferably allow for adjustment/tuning during assembly (in coordination with the biasing means 184, which may be a coil spring, leaf spring, or any other appropriate biasing means).

Figure 3A:
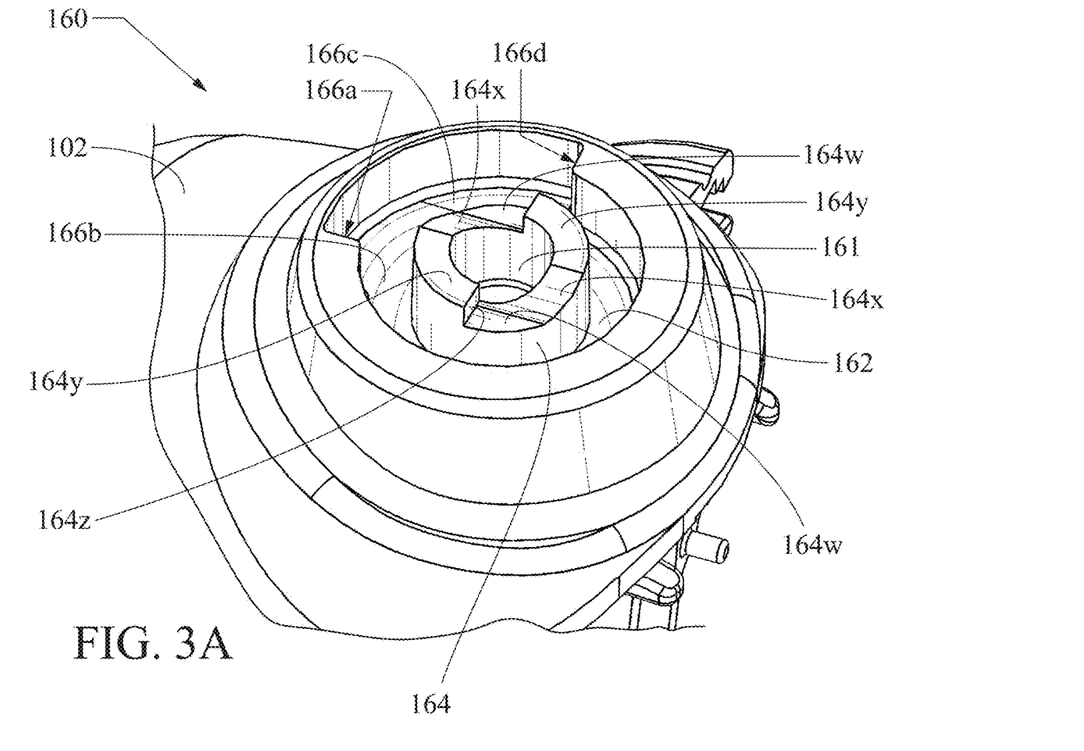
FIG. 3A shows the ramped recessed handle body surface that receives a brake knob.
Figure 3B:
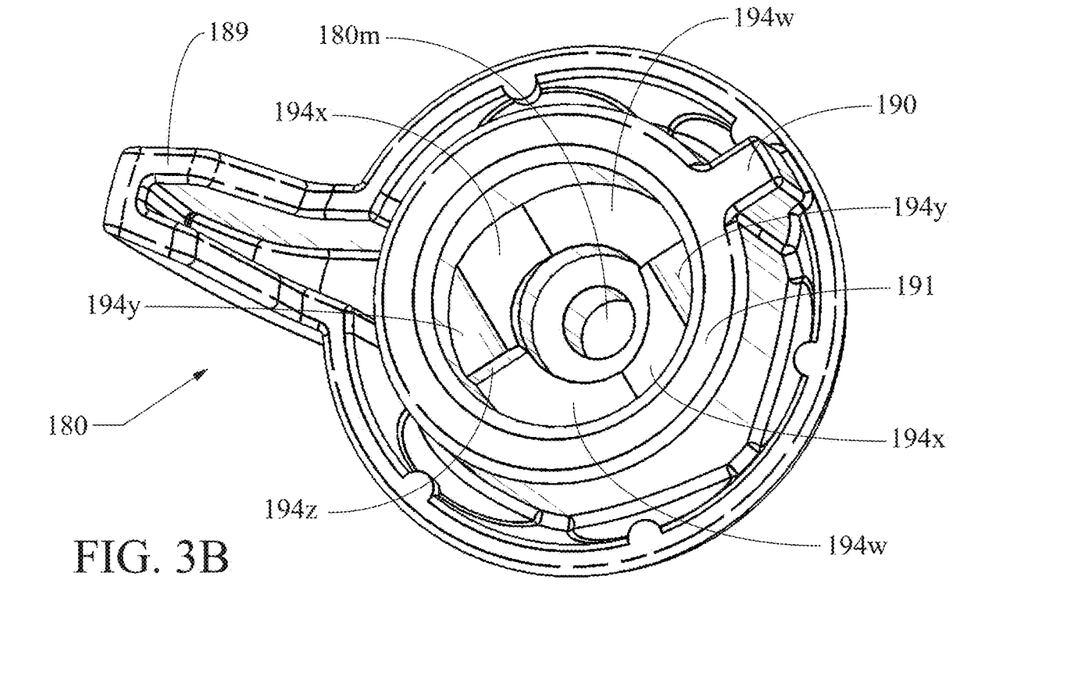
FIG. 3B shows an underside view of the brake knob.
Figure 3C:
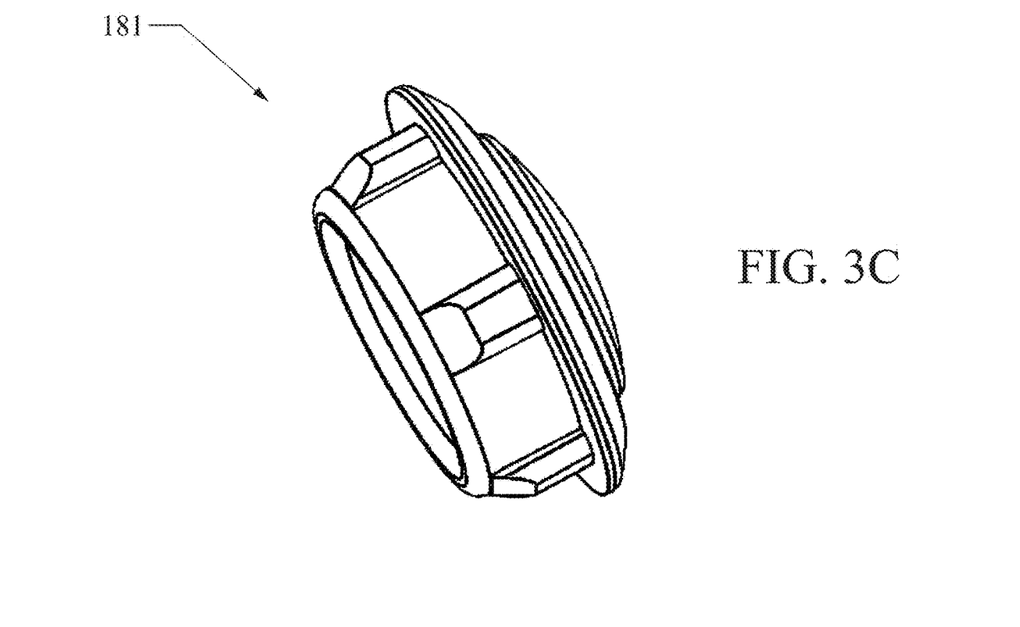
FIG. 3C shows the brake knob cap.
Figure 3D:
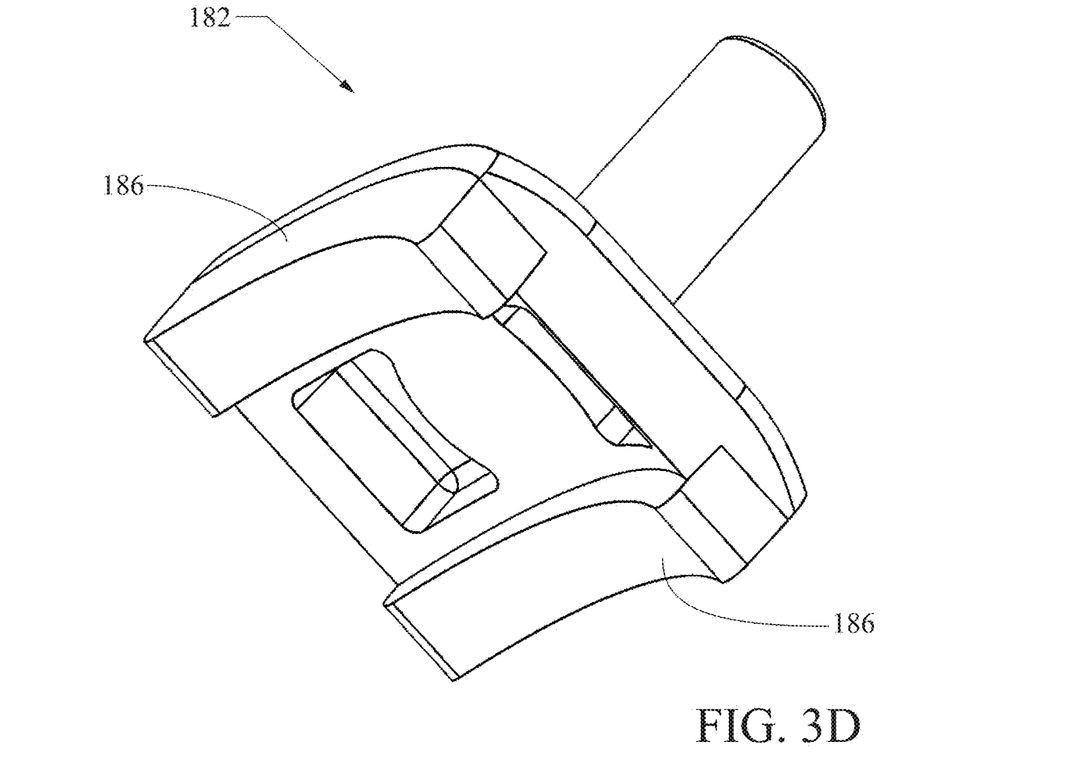
FIG. 3D shows the brake arm with brake shoes.

This operation for engagement/disengagement of the brake arm 182 with the spools is effected by a complementary interface between the underside of the knob 180 (shown in FIG. 3B) and a recessed portion of the handle body housing 102 (shown in FIG. 3A). As will be appreciated by those of skill in the art, these complementary surfaces are contoured and dimensioned to provide a path of motion that will selectably direct the brake arm into contact with, and retract the brake arm from contact with, the spools. Changes in the contours and/or dimensions may be used to increase or decrease the amount of force directed into full-contact engagement between the brake arm and the spools. In the illustrated embodiment, the contact provided by the complementary interface (described in more detail below) may be characterized as light contact, which is enhanced by the bias of the biasing element 184.

Figure 4A:
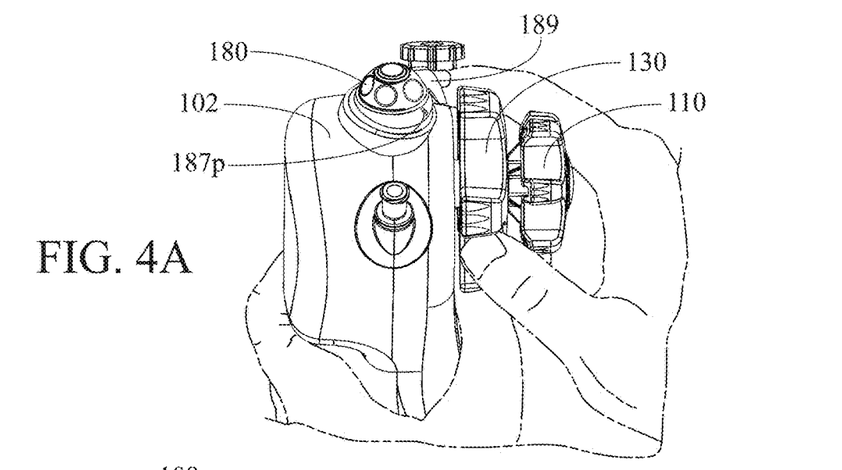
FIGS. 4A-4C depict brake knob actuation states of a brake mechanism.
Figure 4B:
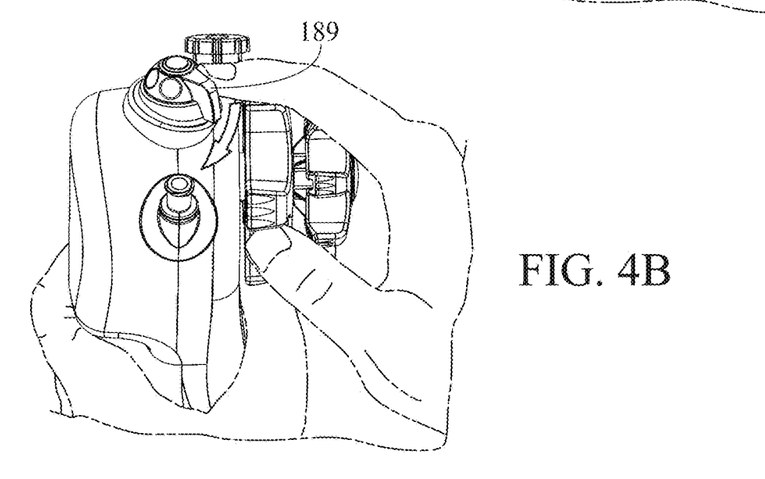
Figure 4C:
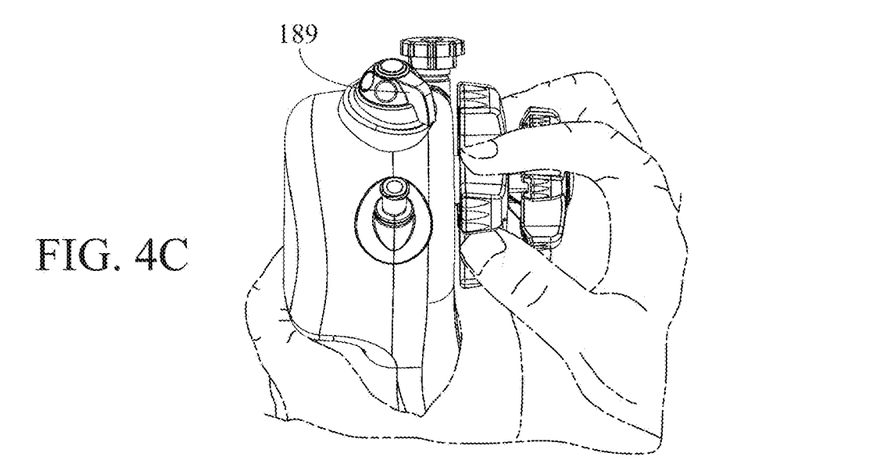

The exact quantitative measurements of the frictional and other forces will vary depending upon the materials of the brake arm (including brake shoes, if present), the spools, the control wires, and the catheter body. However, those of skill in the art will be able to provide and fine-tune this mechanism with reference to the present disclosure. At the very least, locked-in engagement of the brake mechanism will hold the spools in place when they are oriented in a manner that deflects the catheter distal end portion 160, resisting any implicit/natural tendency of the catheter or other elements to straighten the catheter body or otherwise move. In certain preferred embodiments, an operator may still rotate one or both control wheels 110, 130 in a manner moving one or both spools—even while engaged with the brake—without damaging any components, but such an operation will require exerting greater force than operating the wheels and spools without the brake engaged. For example, this may allow a user to deflect the catheter, lock in the brake (e.g., as shown in FIGS. 4A-4C), direct a tool through a working channel of the catheter, then—with the brake engaged—move (e.g., "fine tune") the location of the deflected catheter end to a desired location. However, in preferred embodiments the locked-in deflected end will not move unless the operator actuates one or both control wheels with sufficient force to overcome the frictional engagement of the brake mechanism with the spool(s).

The brake mechanism's operation, including by complementary interaction of ramped surfaces, may be understood with reference to FIGS. 2B, 3A, 3B, 3D, and 4A-4C. The brake arm 182 shown in FIG. 3D includes a post 182*a*, a foot 182*b*, and the brake shoes 186, where the illustrated embodiment shows the foot and shoes as being curved to conform in a matching complementary manner with the outer circumferential surface of the spools so as to fully frictionally engage therewith. The brake arm post 182*a* passes through a central opening 161 of the knob-receiving recess 160 and is received rotatably into the knob 180 so that movement of the knob along the post's longitudinal central axis will move the arm reciprocally along that axis (which is also the central rotational axis of the knob).

The recess 160 of the housing 102 includes an outer track, a channel 162, and an inner annulus 164, which allow transit interface therewith, respectively, of a camming tab 190, a ring 191, and an inner track within the ring. When the knob 180 is engaged into the recess 160, the camming tab 190 rides along a ramped surface 166*c* and planar surface 166*b* of the outer track between end termini 166*a*, 166*d*. At the same time ramped and planar surfaces of the inner annulus 164 will complementarily engage ramped and planar surfaces of the knob's inner track. The inner annulus 164 includes radially-opposite lower planar surfaces 164*w* that are separated from higher planar surfaces 164*y* by intervening ramped surfaces 164*x*. This structure provides a stop-surface 164*z* that are shown as substantially or exactly perpendicular to the lower planar surfaces 164*w*. On the ring 191, the inner track includes radially-opposite lower planar surfaces 194*w* that are separated from higher planar surfaces 194*y* by intervening ramped surfaces 194*x*. This structure provides a stop-surface 194*z* that are shown as substantially or exactly perpendicular to the lower planar surfaces 194*w*.

In a first, unlocked/unbraked, state, with the knob 180 in the position shown in FIG. 4A, the brake arm (including its brake shoe(s), if present) is not contacting the spools, so that the operator can freely rotate the control wheels and spools to deflect the catheter. An advantage of the present embodiments is also shown in FIGS. 4A-4B, where the operator can use a single finger to actuate/rotate the knob 180 without releasing or changing grip on the control wheels 110, 130. Stated differently, the knob is located and oriented to be reachable by a single digit of a user's hand, other digits of which are simultaneously operably grasping one or both control wheel(s). Internally, in the unlocked/unbraked state, the camming tab 190 contacts both the housing's planar surface 166*b* and the unbraked terminal end 166*a* of the housing's outer track, where—in this position—the knob holds the attached brake arm away from the spools (where the knob's cap 181 is at its greatest distance from the housing 102). This unbraked state is aided or at least complemented by the interaction of the opposed, but complementary engagement of ramped and planar surfaces of the knob's inner track with ramped and planar surfaces of the housing's inner annulus. Specifically, the knob's higher planar surfaces 194*y* contact the inner annulus higher surfaces 164*y*. An externally visible portion of the housing may include visual indicia (e.g., showing an image and/or wording for unbraked/unlocked) corresponding to the position of the exterior knob tab 189 in this unbraked state.

In a second, locked/braked, state, with the knob 180 in the position shown in FIG. 4C, the brake arm (including its brake shoe(s), if present) is contacting the spools in the manner shown in FIGS. 2B-2C, so that the control wheels and spools are held in place and a deflected position of the catheter is retained without the operator having to hold one or both control wheels in place. Internally, in the locked/braked state, the camming tab 190 contacts both the housing's ramped surface 166*c* and the braked terminal end 166*d* of the housing's outer track. In this position, the knob 180 moves the attached brake arm 182 toward the spools (so that the knob's cap 181 is at its nearest distance from the housing 102, and the biasing means 184 operates to press/bias the brake arm toward/against the spool(s)). This braked state is aided or at least complemented by the interaction of the opposed, but complementary engagement of ramped and planar surfaces of the knob's inner track with ramped and planar surfaces of the housing's inner annulus. Specifically, the knob's higher planar surfaces 194*y* contact the inner annulus lower planar surfaces 164*w*. An externally visible portion of the housing may include visual indicia (e.g., showing an image and/or wording for braked/locked) corresponding to the position of the exterior knob tab 189 in this braked state, where FIG. 4A shows—by way of nonlimiting example—an iconographic image of a closed lock that is aligned with the outer knob tab 189 in FIG. 4C, and the locked/unlocked icons 187*p*/187*q* in FIG. 2C.

The combination of contact between the knob 180 and housing recess 160 with the biasing means 184 may also provide, in certain embodiment, tactile and/or auditory feedback for braking/locking engagement and/or for unbraking/unlocking disengagement. For example, as an operator actuates the knob 180 by rotation from the position shown in FIG. 4A to the position shown in FIG. 4C, the operator may feel and/or hear a "click" as the tab 190 moves into seated contact against the braked terminal end 166*d* of the housing's outer track. Similarly, when an operator disengages the brake mechanism by rotating the knob 180 from the position shown in FIG. 4C to the position shown in FIG. 4A, the operator may feel and/or hear a "click" as the tab 190 moves into seated contact against the unbraked terminal end 166*a* of the housing's outer track. One or more of the visual, tactile, and auditory indicia will provide an operator with increased confidence and security regarding the operative state of the distal catheter end portion 160 (e.g., whether it is freely moving/deflectable, or is substantially locked into a particular conformation). As noted above, being substantially locked into place by frictional contact of the brake arm with the spool(s) may still—in some embodiments—permit an operator to exert extra force and still move the control wheels in a limited manner that may be used to fine-tune position/conformation of the distal catheter end portion 160.

With regard to particular construction materials those of skill in the art, when informed by the present disclosure, will appreciate that many variant options are possible for exact dimensions and construction materials of the brake arm, biasing means, brake shoe(s)(if present), spool outer circumferential surfaces, etc. An effective brake mechanism assembly according to the presently disclosed inventive embodiments will provide a combination of normal force and dynamic friction that offer the braking functionality described herein. In one embodiment, the brake arm 182 may be constructed of polycarbonate, and the brake shoe(s) 186 may be constructed of an elastic high-friction moldable polymer (e.g., Versaflex™ OM 1040X, available from PolyOne of Avon Lake, Ohio). The spools contacted by the brake shoe(s) may be made of HDPE (high-density polyethylene) or nylon (e.g., Nylon™ 1000N), which will provide good braking contact as well as provide the mechanical strength and other properties needed for fine control of the control wires. The surface of the spool(s) and/or brake shoe(s) may also be textured to enhance frictional contact.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. References herein to any industry standards (e.g., ASTM standards, and product identifiers such as particular polymers, as well as any trademarks) are defined as complying with the currently published standards and corresponding quantitatively and qualitatively defined specifications as of the original filing date of this disclosure unless expressly otherwise defined herein. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A steerable catheter with a braking mechanism, the steerable catheter comprising:
   a proximal handle body from which extends distally an elongate steerable catheter body including a deflectable distal catheter body end;
   where the proximal handle body includes:
      at least a first control wheel in mechanical communication, via a first spool, with the distal catheter body end, where the at least a first control wheel and the first spool are rotatable around a common control wheel axis;
      a brake knob mounted rotatingly to the proximal handle body and configured to rotate around a brake knob axis that is non-coaxial with the control wheel axis;
      a brake arm in mechanical communication with the brake knob and disposed between the brake knob and the first spool, said brake arm including at least one spool-engagement surface; and
      ramped and planar handle body surfaces that complementarily interface with ramped and planar brake knob surfaces such that
         in a first brake-actuation knob position the at least one spool-engagement surface does not contactingly engage the first spool, and
         in a second brake-actuation knob position the at least one spool-engagement surface does contactingly engage the first spool, configured such that movement between the first and second brake-actuation knob positions is along the brake knob axis.

2. The steerable catheter of claim 1, where the at least one spool-engagement surface is biased away from the knob and toward the control wheel axis.

3. The steerable catheter of claim 2, where the brake knob axis is orthogonal to the control wheel axis.

4. The steerable catheter of claim 1, where the knob includes a stop tab, which—when the knob is disposed in the first brake-actuation knob position—contacts a first stop-surface of the handle body, and which—when the knob is disposed in the second brake-actuation knob position—contacts a second stop-surface of the handle body.

5. The steerable catheter of claim 4, where the knob's stop tab contacts at least one of the ramped and planar handle body surfaces between the first stop-surface and the second stop-surface.

6. The steerable catheter of claim 4, where the knob is confined to a mechanically-limited arc of rotation, one end of which arc corresponds to the knob being in the first brake-actuation knob position and the stop tab contacting the first stop-surface, and an opposite end of which arc corresponds to the knob being in the second brake-actuation knob position and the stop tab contacting the second stop-surface.

7. The steerable catheter of claim 1, where the at least one spool-engagement surface is configured as at least one brake shoe.

8. The steerable catheter of claim 1, where the knob is located in a position such that it is reachable by a digit of a user's hand when other digits of said hand are simultaneously operably grasping the at least a first control wheel.

9. The steerable catheter of claim 1, constructed such that when the knob is in the second brake-actuation knob position, the at least one spool-engagement surface contacting engagement with the first spool provides sufficient friction to inhibit said spool from rotating freely, and thereby corresponds to inhibiting change in a deflected state of the distal catheter body end.

10. The steerable catheter of claim 1, where a coil spring biases the at least one spool-engagement surface away from the knob and toward the control wheel axis with a predetermined amount of force such that the at least one spool-engagement surface contacting engagement with the first spool provides sufficient friction to inhibit said spool from rotating freely inhibits change in a deflected state of the distal catheter body end.

11. A steerable catheter with a brake mechanism, the brake mechanism comprising:
- a knob mounted to a catheter handle body, said knob being rotatable, relative to the handle body, around a knob axis;
- where the catheter handle body includes at least one steering control spool rotatable around a spool axis that is orthogonal to the knob axis;
- a handle ramped surface separated from a handle stop-surface, where a handle-contacting knob surface is movable across the handle ramped surface and not movable past the handle stop-surface; and
- a frictional braking element in mechanical communication, along the knob axis, with the knob, said braking element disposed adjacent the at least one spool and actuatable into and out of contact with a contact surface of the at least one spool upon rotation of the knob around the knob axis.

12. The steerable catheter of claim 11, where the braking element is biased away from the knob and toward the at least one spool.

13. The steerable catheter of claim 11, where the handle-contacting knob surface includes a knob ramped surface and includes a knob stop-surface substantially perpendicular to the knob ramped surface.

14. The steerable catheter of claim 13, where a first actuation state corresponds to the knob stop-surface contacting the handle stop-surface and the frictional braking element contacting the at least one spool with sufficient force to inhibit spool rotation.

15. The steerable catheter of claim 14, where the braking element is biased away from the knob and toward the spool.

16. The steerable catheter of claim 15, where the knob has a mechanically-limited arc of rotation, one end of which arc is defined by the knob stop-surface contacting the handle stop-surface, and an opposite end of which arc corresponding with the braking element not inhibiting rotation of the at least one spool.

17. The steerable catheter of claim 14, constructed where contacting the at least one spool with sufficient force to inhibit spool rotation prevents rotation of the at least one spool relative to the braking element.

18. The steerable catheter of claim 11, where the at least one spool includes at least one face surface intersecting the spool axis and at least one circumferential surface that includes or is included by the contact surface.

19. The steerable catheter of claim 11, where the knob is located in a position such that it is reachable and rotatable by a digit of a user's hand when other digits of said hand are simultaneously operably contacting at least a first control wheel, which control wheel shares a common rotational axis with the at least one spool.

20. The steerable catheter of claim 11, where a braking element portion, actuatable into and out of contact with the contact surface of the at least one spool, comprises a brake shoe that is biased away from the knob and toward the at least one spool by a coil spring disposed between the brake shoe and the catheter handle body.

* * * * *